(12) United States Patent
Yaron et al.

(10) Patent No.: US 8,034,016 B2
(45) Date of Patent: Oct. 11, 2011

(54) FLOW REGULATING IMPLANTS AND METHODS OF IMPLANTING

(75) Inventors: Ira Yaron, Har Adar (IL); Elie Dahan, Johannesburg (ZA)

(73) Assignee: Optonol, Ltd., Neve Ilan (IL)

( * ) Notice: Subject to any disclaimer, the term of this patent is extended or adjusted under 35 U.S.C. 154(b) by 0 days.

(21) Appl. No.: 11/952,754

(22) Filed: Dec. 7, 2007

(65) Prior Publication Data

US 2008/0077071 A1 Mar. 27, 2008

Related U.S. Application Data

(62) Division of application No. 10/875,571, filed on Jun. 25, 2004, now Pat. No. 7,862,531.

(51) Int. Cl.
*A61M 5/00* (2006.01)

(52) U.S. Cl. .................... 604/8; 604/9; 604/10; 604/30; 604/43; 604/521; 604/57; 604/60; 604/104; 604/175; 604/239; 604/264; 604/265; 604/266; 604/541

(58) Field of Classification Search .......... 604/8–10, 604/30, 43, 521, 57, 60, 104, 175, 239, 264–266, 604/541

See application file for complete search history.

(56) References Cited

U.S. PATENT DOCUMENTS

| 15,192 | A | 6/1856 | Peale |
|---|---|---|---|
| 274,447 | A | 3/1883 | Kennish |
| 733,152 | A | 7/1903 | Chisholm |
| 1,388,172 | A | 8/1921 | Craddock |
| 2,431,587 | A | 11/1947 | Schnee |
| 2,555,076 | A | 5/1951 | Crossley |
| 2,867,213 | A | 6/1957 | Thomas, Jr. |
| 3,159,161 | A | 12/1964 | Ness |
| 3,272,204 | A | 9/1966 | Artandi et al. |
| 3,310,051 | A | 3/1967 | Schulte |
| 3,333,588 | A | 8/1967 | Schulte |
| 3,421,509 | A | 1/1969 | Fiore |
| 3,530,860 | A | 9/1970 | Majoros |
| 3,589,401 | A | 6/1971 | Harding |
| 3,788,327 | A | 1/1974 | Donowitz et al. |

(Continued)

FOREIGN PATENT DOCUMENTS

EP 102747 A 3/1984

(Continued)

OTHER PUBLICATIONS

Prata, Jr., et al., "In Vitro and In Vivo Flow Characteristics of Glaucoma Drainage Implants," Ophthalmology, vol. 102, No. 5.

(Continued)

*Primary Examiner* — Melanie Hand
*Assistant Examiner* — Ginger T Chapman
(74) *Attorney, Agent, or Firm* — Kenyon & Kenyon LLP

(57) ABSTRACT

A flow regulating implant is provided with one or more grooves for allowing fluid flow. One or more grooves may have a constant or varying cross-section along its length. One or more grooves may have in it biodegradable material, absorbable material, and/or threads or sutures. A resilient band or coating may be placed around the implant or one or more grooves, to act as a pressure regulator. The implant may have a side projection, such as a side pin, for engaging tissue. The implant may comprise two or more parts that are held at a distance from each other to allow fluid flow between the parts.

15 Claims, 5 Drawing Sheets

U.S. PATENT DOCUMENTS

| | | | |
|---|---|---|---|
| 3,884,238 A | 5/1975 | O'Malley et al. | |
| 3,890,976 A | 6/1975 | Bazell et al. | |
| 3,913,584 A | 10/1975 | Walchle et al. | |
| 3,915,172 A | 10/1975 | Wichterle et al. | |
| 3,938,529 A | 2/1976 | Gibbons | |
| 3,957,035 A | 5/1976 | Chassaing | |
| 3,976,077 A | 8/1976 | Kerfoot, Jr. | |
| 4,037,604 A | 7/1977 | Newkirk | |
| 4,142,526 A | 3/1979 | Zaffaroni et al. | |
| 4,153,058 A | 5/1979 | Nehme | |
| 4,175,563 A | 11/1979 | Arenberg et al. | |
| 4,290,426 A | 9/1981 | Luschen et al. | |
| 4,299,227 A | 11/1981 | Lincoff | |
| 4,303,063 A | 12/1981 | Stahl | |
| 4,402,681 A | 9/1983 | Hass et al. | |
| 4,457,757 A | 7/1984 | Molteno | |
| 4,474,569 A | 10/1984 | Newkirk | |
| 4,521,210 A * | 6/1985 | Wong | 604/8 |
| 4,526,343 A | 7/1985 | d'Agostino et al. | |
| 4,538,611 A | 9/1985 | Keiman | |
| 4,554,918 A | 11/1985 | White | |
| 4,563,779 A | 1/1986 | Kelman | |
| 4,578,058 A | 3/1986 | Grandon | |
| 4,587,954 A | 5/1986 | Haber | |
| 4,598,705 A | 7/1986 | Lichtenberger | |
| 4,604,087 A | 8/1986 | Joseph | |
| 4,634,418 A | 1/1987 | Binder | |
| 4,645,493 A | 2/1987 | Ferrando et al. | |
| 4,660,546 A | 4/1987 | Herrick et al. | |
| 4,692,142 A | 9/1987 | Dignam et al. | |
| 4,722,724 A | 2/1988 | Schocket | |
| 4,750,901 A | 6/1988 | Molteno | |
| 4,750,971 A | 6/1988 | Maas et al. | |
| 4,751,926 A | 6/1988 | Sasaki | |
| 4,781,675 A | 11/1988 | White | |
| 4,787,885 A | 11/1988 | Binder | |
| 4,808,183 A | 2/1989 | Panje | |
| 4,813,941 A | 3/1989 | Shea | |
| 4,826,478 A | 5/1989 | Schocket | |
| 4,863,457 A | 9/1989 | Lee | |
| 4,886,488 A | 12/1989 | White | |
| 4,909,783 A | 3/1990 | Morrison | |
| 4,915,684 A | 4/1990 | MacKeen et al. | |
| 4,934,363 A | 6/1990 | Smith et al. | |
| 4,936,825 A | 6/1990 | Ungerleider | |
| 4,942,875 A | 7/1990 | Hlavacek et al. | |
| 4,946,436 A | 8/1990 | Smith | |
| 4,959,048 A | 9/1990 | Seder et al. | |
| 4,964,850 A | 10/1990 | Bouton et al. | |
| 4,968,296 A | 11/1990 | Ritch et al. | |
| 5,000,731 A | 3/1991 | Wong | |
| 5,041,081 A | 8/1991 | Odrich | |
| 5,053,040 A | 10/1991 | Goldsmith, III | |
| 5,064,417 A | 11/1991 | Andreussi | |
| 5,071,408 A | 12/1991 | Ahmed | |
| 5,073,163 A | 12/1991 | Lippman | |
| 5,092,837 A | 3/1992 | Ritch et al. | |
| 5,098,393 A | 3/1992 | Amplatz et al. | |
| 5,098,438 A | 3/1992 | Siepser | |
| 5,106,367 A | 4/1992 | Ureche et al. | |
| 5,127,901 A | 7/1992 | Odrich | |
| 5,139,502 A | 8/1992 | Berg et al. | |
| 5,147,370 A | 9/1992 | McNamara et al. | |
| 5,167,620 A | 12/1992 | Ureche et al. | |
| 5,171,213 A | 12/1992 | Price, Jr. | |
| 5,171,270 A | 12/1992 | Herrick | |
| 5,178,604 A | 1/1993 | Baerveldt et al. | |
| 5,190,552 A | 3/1993 | Kelman | |
| 5,207,660 A | 5/1993 | Lincoff | |
| 5,217,486 A | 6/1993 | Rice et al. | |
| 5,221,278 A | 6/1993 | Linkwitz et al. | |
| 5,242,449 A | 9/1993 | Zaleski | |
| 5,283,063 A | 2/1994 | Freeman | |
| 5,300,020 A | 4/1994 | L'Esperance, Jr. | |
| 5,318,558 A | 6/1994 | Linkwitz et al. | |
| 5,322,504 A | 6/1994 | Doherty et al. | |
| 5,326,345 A | 7/1994 | Price, Jr. | |
| 5,338,291 A | 8/1994 | Speckman et al. | |
| 5,342,370 A | 8/1994 | Simon et al. | |
| 5,346,464 A | 9/1994 | Camras | |
| 5,355,871 A | 10/1994 | Hurley et al. | |
| 5,358,492 A | 10/1994 | Feibus | |
| 5,360,398 A | 11/1994 | Grieshaber et al. | |
| 5,360,399 A | 11/1994 | Stegmann | |
| 5,370,607 A | 12/1994 | Memmen | |
| 5,372,577 A | 12/1994 | Ungerleider | |
| 5,380,290 A | 1/1995 | Makower et al. | |
| D356,867 S | 3/1995 | Krupin | |
| 5,397,300 A | 3/1995 | Baerveldt et al. | |
| 5,403,323 A | 4/1995 | Smith | |
| RE34,998 E | 7/1995 | Langerman | |
| 5,433,701 A * | 7/1995 | Rubinstein | 604/8 |
| 5,433,714 A | 7/1995 | Bloomberg | |
| 5,451,229 A | 9/1995 | Geuder et al. | |
| 5,454,796 A | 10/1995 | Krupin | |
| 5,476,445 A | 12/1995 | Baerveldt et al. | |
| 5,494,484 A | 2/1996 | Feingold | |
| 5,520,631 A | 5/1996 | Nordquist et al. | |
| 5,522,845 A | 6/1996 | Wenstrom, Jr. | |
| 5,558,629 A | 9/1996 | Baerveldt et al. | |
| 5,558,630 A * | 9/1996 | Fisher | 604/8 |
| 5,601,094 A | 2/1997 | Reiss | |
| 5,616,118 A | 4/1997 | Ahmed | |
| 5,626,558 A * | 5/1997 | Suson | 604/8 |
| 5,626,559 A | 5/1997 | Solomon | |
| 5,660,205 A | 8/1997 | Epstein | |
| 5,674,286 A | 10/1997 | D'Alessio et al. | |
| 5,702,414 A | 12/1997 | Richter et al. | |
| 5,704,907 A | 1/1998 | Nordquist et al. | |
| 5,709,698 A | 1/1998 | Adams et al. | |
| 5,713,844 A | 2/1998 | Peyman | |
| 5,720,760 A | 2/1998 | Becker et al. | |
| 5,741,292 A | 4/1998 | Mendius | |
| 5,800,376 A | 9/1998 | Watson et al. | |
| 5,807,240 A | 9/1998 | Muller et al. | |
| 5,865,831 A | 2/1999 | Cozean et al. | |
| 5,868,697 A | 2/1999 | Richter et al. | |
| 5,879,319 A * | 3/1999 | Pynson et al. | 604/8 |
| 5,893,837 A | 4/1999 | Eagles et al. | |
| 5,968,058 A | 10/1999 | Richter et al. | |
| 6,004,302 A | 12/1999 | Brierley | |
| 6,007,510 A | 12/1999 | Nigam | |
| 6,007,511 A | 12/1999 | Prywes | |
| 6,050,970 A | 4/2000 | Baerveldt | |
| 6,102,045 A | 8/2000 | Nordquist | |
| 6,168,575 B1 | 1/2001 | Soltanpour | |
| 6,186,974 B1 | 2/2001 | Allan et al. | |
| 6,203,513 B1 | 3/2001 | Yaron et al. | |
| 6,221,078 B1 | 4/2001 | Bylsma | |
| 6,245,077 B1 | 6/2001 | East et al. | |
| 6,264,625 B1 | 7/2001 | Rubenstein et al. | |
| 6,280,468 B1 | 8/2001 | Schachar | |
| 6,299,640 B1 | 10/2001 | Schachar | |
| 6,450,984 B1 | 9/2002 | Lynch et al. | |
| 6,730,056 B1 * | 5/2004 | Ghaem et al. | 604/9 |
| 7,008,396 B1 * | 3/2006 | Straub | 604/8 |
| 7,041,077 B2 | 5/2006 | Shields | |
| 7,207,965 B2 | 4/2007 | Simon | |
| 7,862,531 B2 * | 1/2011 | Yaron et al. | 604/8 |
| 2001/0000527 A1 * | 4/2001 | Yaron et al. | 604/9 |
| 2004/0015140 A1 | 1/2004 | Shields | |
| 2004/0088048 A1 * | 5/2004 | Richter et al. | 623/4.1 |
| 2004/0147870 A1 | 7/2004 | Burns et al. | |
| 2005/0119601 A9 | 6/2005 | Lynch et al. | |
| 2005/0266047 A1 | 12/2005 | Tu et al. | |
| 2006/0069340 A1 * | 3/2006 | Simon | 604/8 |

FOREIGN PATENT DOCUMENTS

| | | |
|---|---|---|
| EP | 228185 A | 7/1987 |
| EP | 606188 | 7/1994 |
| EP | 1310222 A2 * | 5/2003 |
| EP | 1 310 222 A | 5/2008 |
| FR | 2 721 499 A | 12/1995 |
| FR | 2 757 068 | 6/1998 |
| JP | 63-305860 | 12/1988 |
| JP | 3-292953 | 12/1991 |
| JP | 5-115502 | 5/1993 |

| | | |
|---|---|---|
| JP | 5-502811 | 5/1993 |
| JP | 8-155540 | 6/1996 |
| SU | 1191227 | 11/1985 |
| SU | 1797884 | 2/1993 |
| WO | WO 91/08784 | 6/1991 |
| WO | WO 92/00112 | 1/1992 |
| WO | WO 93/20783 | 10/1993 |
| WO | WO 94/02081 | 2/1994 |
| WO | 94/06503 A1 | 3/1994 |
| WO | WO 94/09837 | 4/1994 |
| WO | WO 94/13234 | 6/1994 |
| WO | WO 94/17755 | 8/1994 |
| WO | WO 94/21443 | 8/1994 |
| WO | WO 95/35078 | 12/1995 |
| WO | WO 96/03944 | 2/1996 |
| WO | WO 96/20742 | 7/1996 |
| WO | WO 96/36377 | 11/1996 |
| WO | WO 98/30181 | 1/1998 |
| WO | WO 99/26567 | 6/1999 |
| WO | 00/64393 A1 | 11/2000 |
| WO | WO 00/72788 | 12/2000 |
| WO | 2007/087061 A2 | 8/2007 |
| WO | 2008/005873 A2 | 1/2008 |

OTHER PUBLICATIONS

Krupin, et al., "Drainage Implants", Glaucoma, edited by Kaufman et al., Section VII.

Sidoti, et al., "Glaucoma Drainage Implants", Current Opinion in Ophthamology.

Middleton, et al., "Synthetic Biodegradable Polymers as Medical Devices", Medical Plastics and Biomaterials Magazige MPB Article Index, Mar. 1998, 14 pages.

Communication Relating to the Results of the Partial International Search, from PCT/US2009/033049, mailed May 15, 2009.

* cited by examiner

FLOW REGULATING IMPLANTS AND METHODS OF IMPLANTING

CROSS-REFERENCE TO RELATED APPLICATIONS

This application is a division of application Ser. No. 10/875,571 filed Jun. 25, 2004 now U.S. Pat. No. 7,862,531.

FIELD OF THE INVENTION

The invention relates generally to flow regulating implants, for example ophthalmic implants for treatment of glaucoma.

BACKGROUND OF THE INVENTION

U.S. Pat. No. 5,868,697 discloses devices and methods for regulating fluid flow. The devices and methods are useful, for example, in the treatment of glaucoma, by providing for the flow of aqueous humor from the eye to reduce intraocular pressure (IOP). The devices and methods disclosed in that patent are expressly incorporated by reference into this specification.

As with the devices and methods disclosed in U.S. Pat. No. 5,868,697, the devices and methods disclosed herein are also for regulating fluid flow. The devices and methods disclosed herein are useful, for example, in the treatment of glaucoma, by providing for the flow of aqueous humor from the eye to reduce intraocular pressure (IOP).

SUMMARY OF THE INVENTION

In certain embodiments, the invention is directed to an improved flow regulating implant that has one or more grooves for allowing fluid flow.

In certain embodiments, one or more grooves may have a constant cross-section along its length.

In certain embodiments, one or more grooves may have a varying cross-section along its length. For example, one or more grooves may be tapered, as a funnel. The wider end may be at the inlet end or the outlet end.

In certain embodiments, one or more grooves may have in it biodegradable material, absorbable material, and/or threads or sutures.

In certain embodiments, a resilient band or coating may be placed around the implant or one or more grooves, to act as a pressure regulator.

In certain embodiments, in addition to one or more grooves, the implant may have a tube passage running through it. The tube passage may have in it biodegradable material, absorbable material, and/or threads or sutures.

In certain embodiments, the implant may have a side projection, such as a side pin, for engaging tissue. The side projection or pin may be useful for resisting rotation and/or firmly holding the implant within the tissue.

In certain embodiments, the implant may comprise two or more parts that are held at a distance from each other to allow fluid flow between the parts.

DETAILED DESCRIPTION

Figure 1:
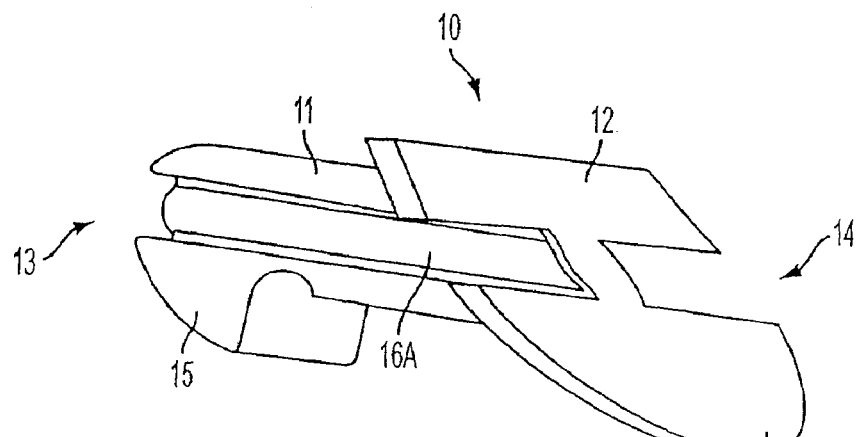
FIG. 1 is a perspective view of a first embodiment of a flow regulating implant.
Figure 2:
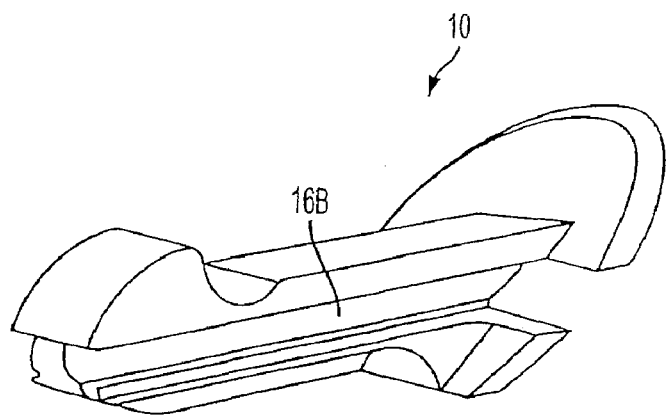
FIG. 2 is an alternative perspective view of the flow regulating implant of FIG. 1.
Figure 3:
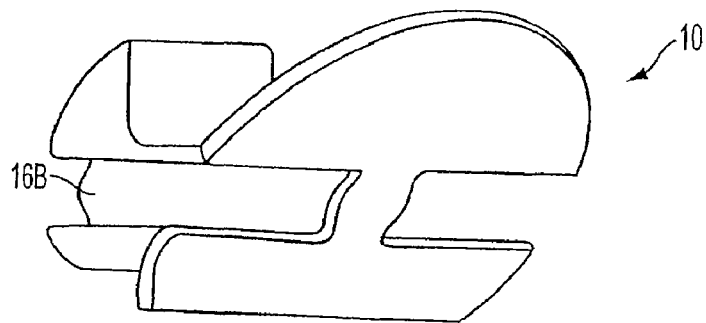
FIG. 3 is an alternative perspective view of the flow regulating implant of FIG. 1.

FIGS. 1 to 3 illustrate a first embodiment of a flow regulating implant. The illustrated implant is in the form of an intraocular implant 10. The implant 10 comprises a shaft 11 and a flange (or plate or disk) 12. The cross-section of the shaft may take any suitable shape, for example square, rectangular, ellipsoidal, circular, or an irregular shape. In this illustrated embodiment, the plane of the flange 12 forms an angle with the shaft 11 that corresponds generally to the angle between the surface of the sclera of an eye and the intended axis of insertion of the implant 10. The flange 12 limits the depth of insertion and stabilizes the device. The angling of the flange 12 helps limit or prevent rotation of the device. In certain applications, it may be desired to remove the device, in which case the flange may be used for that purpose.

The implant 10 has an inlet end 13 and an outlet end 14. The flange 12 is connected to the shaft 11 at the outlet end 14 of the implant 10. The implant 10 may have one or more retention projections 15 for retaining the implant 10 after insertion. The retention projection(s) 15 may take any suitable form.

In the illustrated embodiment, the shaft 11 has a rounded tip at the inlet end 13 of the implant 10. It will be appreciated that the tip may take other suitable forms. For example, the tip may be a needle-like tip formed by a beveled surface, angled sharply for easy insertion into the eyeball.

The implant 10 has two side grooves 16A, 16B. In the illustrated embodiment, the side grooves 16A, 16B extend the full length of the implant 10, from the inlet end 13 to the outlet end 14. The side grooves 16A, 16B are in the side of the shaft 11 and extend through the flange 12.

An implant in accordance with the invention may be inserted by methods disclosed in U.S. Pat. No. 5,868,697, incorporated herein by reference. The insertion of the implant is not restricted to those methods. In certain instances, it may be desirable to implant the device such that the flange is located under scleral flap, i.e., a flap of tissue cut from the sclera. In such a method, a scleral flap is carefully cut from the sclera. The cut is preferably not made all the way through the sclera to the anterior chamber. Rather, the cut extends only part way through, to create the scleral flap that can be moved away to expose a place for insertion of the implant. With the scleral flap lifted, the implant is inserted in the intended implantation site, with the flange under the scleral flap. The implantation of the device under a scleral flap may assist in absorption of fluid. It also may assist in retention of the device.

With the device as illustrated in FIGS. 1 to 3, in operation, the grooves 16A, 16B form passageways for fluid to flow from the inlet end 13 toward the outlet end 14 of the implant 10. In the case of an intraocular implant, the aqueous humor in the eye can flow along the grooves from the inlet end 13 toward the outlet end 14.

The grooves 16A, 16B are directly adjacent the tissue into which the implant 10 is implanted. Thus, for example, the scleral tissue of the eye will surround the implant. In this manner, the scleral tissue can function as a valve to control the flow of fluid out of the eye. When the pressure in the anterior chamber is low, the tissue is close around the implant and in the grooves to block or limit the flow of fluid along the grooves. When the pressure in the anterior chamber is elevated, the fluid exerts pressure on the tissue to clear the passageway along the grooves, and fluid will flow along the grooves between the implant device and the tissue.

With the grooves, the aqueous humor flowing out of the anterior chamber is allowed to directly contact the scleral tissue, which allows for direct absorption of the aqueous humor by the sclera. The fluid may be absorbed by the sclera or may flow out, for example underneath the conjunctiva.

The groove(s) may take any suitable form. For example, one or more grooves may be shaped as a funnel, tapering from one end to the other. The wider end may be at the outlet end or the inlet end, depending on the desired application. Other modifications to the size, shape, and/or cross-sectional configuration of the groove(s) may be made.

It will be appreciated that in addition to the flow regulation characteristics, the grooves may serve the additional benefit of limiting or preventing rotation of the device. It will also be appreciated that non-circular cross-sections for the shaft will also help limit or prevent rotation of the device. For example, a cross-section having corners, like a square, rectangular or other polygonal cross-section, will help limit or prevent rotation. In addition, a cross-section with different dimensions in different direction, like an elliptical or rectangular cross-section, will help limit or prevent rotation. The grooves may help to limit or prevent rotation even with an otherwise circular cross-section for the shaft. The tissue in the gutters may help hold the position of the device.

Figure 4:
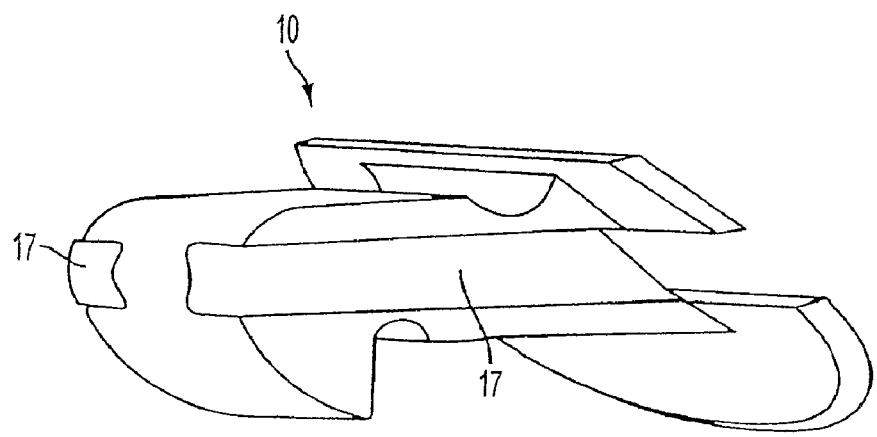
FIG. 4 is a perspective view of the flow regulating implant of FIG. 1, with material in the side grooves.

FIG. 4 illustrates the flow regulating implant of FIG. 1, with material 17 in the side grooves. In this example, the material 17 may be a biodegradable material, an absorbable material, or a material that may be ablated with a laser. Such materials may act to block or limit flow initially and to allow more flow over time. For example, a physician may ablate the laser-ablatable material at some period of time after implantation, or in increments over time. The biodegradable or absorbable material may act to block flow upon initial implantation and to erode or degrade over time to allow more flow. Further descriptions of the use of such materials in flow regulating implants are provided in U.S. Pat. Nos. 6,203,513 and 6,558,342, the disclosures of which are incorporated herein by reference.

Figure 5:
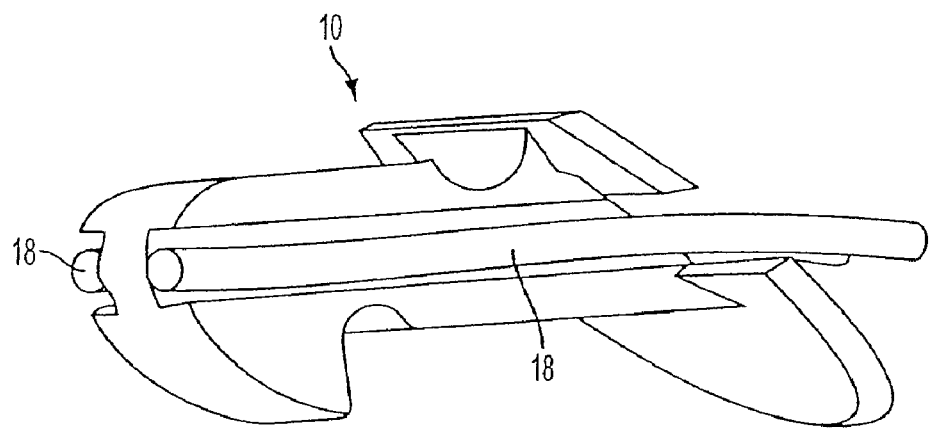
FIG. 5 is a perspective view of the flow regulating implant of FIG. 1, with threads or sutures in the side grooves.

FIG. 5 illustrates the flow regulating implant of FIG. 1, with threads or sutures 18 in the side grooves. The threads or sutures 18 may act to block or limit flow initially and to allow more flow over time. For example, a physician may remove the threads or sutures 18 at some period of time after implantation, or may remove one at a time in increments over time. It will be appreciated that more than one thread or suture 18 may be placed in each groove. Further descriptions of the use of threads or sutures in flow regulating implants are provided in U.S. Pat. No. 6,558,342, the disclosure of which is incorporated herein by reference.

Figure 6:
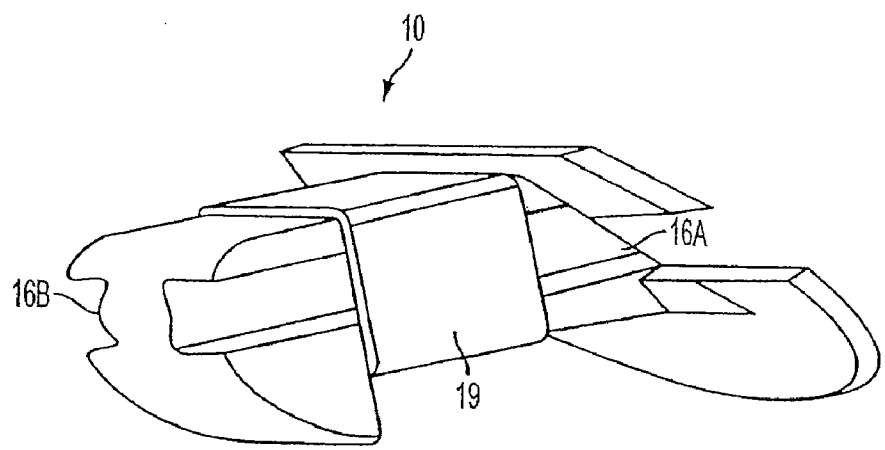
FIG. 6 is a perspective view of the flow regulating implant of FIG. 1, with a flow regulating band or coating around the implant.

FIG. 6 illustrates the flow regulating implant of FIG. 1, with a flow regulating band or coating 19 around the implant. The band or coating 19 may extend over only part of the length of the implant, as illustrated, or, alternatively, it may extend over the full length of the implant. The band or coating 19 may be shaped to extend into the grooves. The band or coating 19 is resilient and acts as valve to control the flow of fluid out of the eye. When the pressure in the anterior chamber is low, the band or coating 19 is close around the implant and in the grooves to block or limit the flow of fluid along the grooves. When the pressure in the anterior chamber is elevated, the fluid exerts pressure on the band or coating 19 to clear the passageway along the grooves, and fluid will flow along the grooves between the implant shaft and the band or coating 19.

Figure 7:
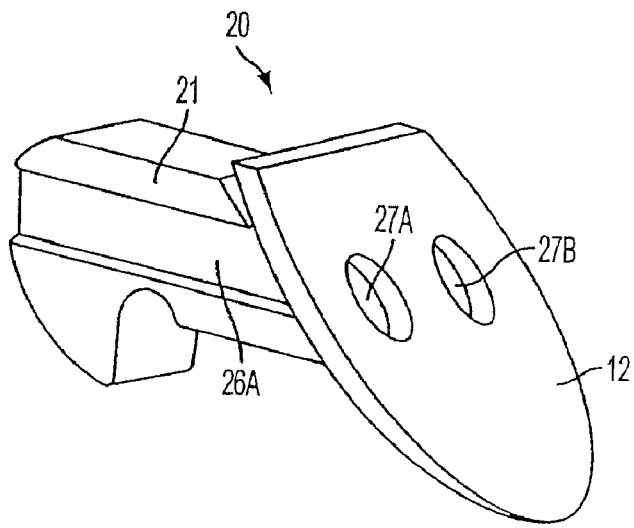
FIG. 7 is a perspective view of an alternative embodiment of a flow regulating implant with side grooves, with holes at the outlet ends of the grooves.

FIG. 7 illustrates another embodiment of a flow regulating implant. This flow regulating implant 20 is similar to the flow regulating implant 10. The flow regulating implant 20 has a shaft 21, a flange 22, and grooves 26A, 26B (groove 26B not shown). In this embodiment, the flange has holes 27A, 27B in it at the outlet ends of the grooves 26A, 26B, respectively. These holes allow the flow of fluid away from the implant.

Figure 8:
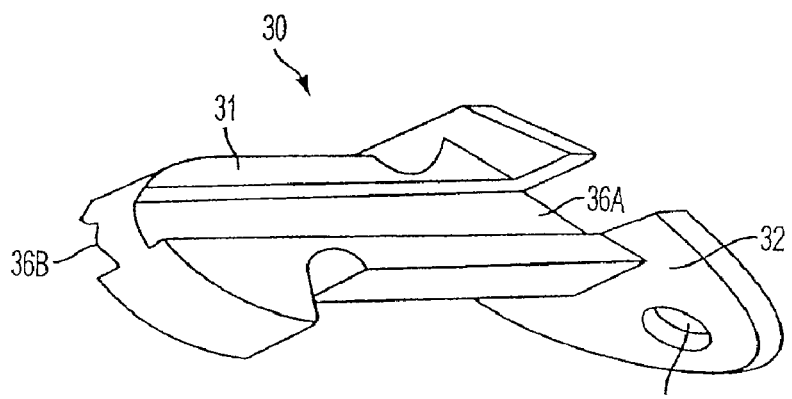
FIG. 8 is a perspective view of another alternative embodiment of a flow regulating implant with side grooves, with a hole in the flange at the outlet end of the implant.

FIG. 8 illustrates another embodiment of a flow regulating implant. This flow regulating implant 30 is similar to the flow regulating implants described above. The flow regulating implant 30 has a shaft 31, a flange 32, and grooves 36A, 36B. In this embodiment, the flange has a hole 38 in it. With this hole, a suture may be used to attach the implant to tissue to fix it in place.

Figure 9:
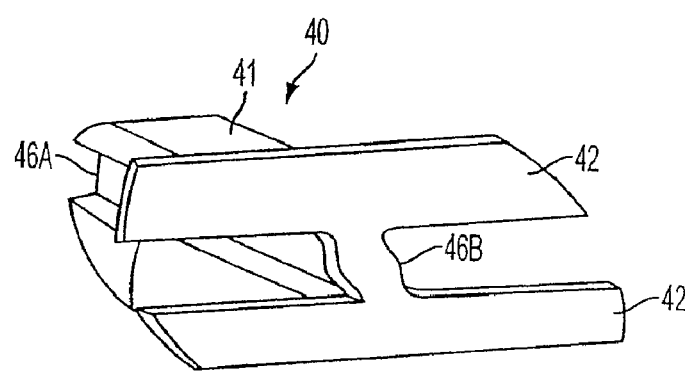
FIG. 9 is a perspective view of an alternative embodiment of a flow regulating implant with side grooves, with an alternative flange design at the outlet end of the implant.

FIG. 9 illustrates a flow regulating implant 40. This flow regulating implant 40 is similar to the flow regulating implants described above. The flow regulating implant 40 has a shaft 41, a flange 42, and grooves 46A, 46B. In this embodiment, the flange 42 has a different shape, which may be useful in certain applications.

Figure 10:
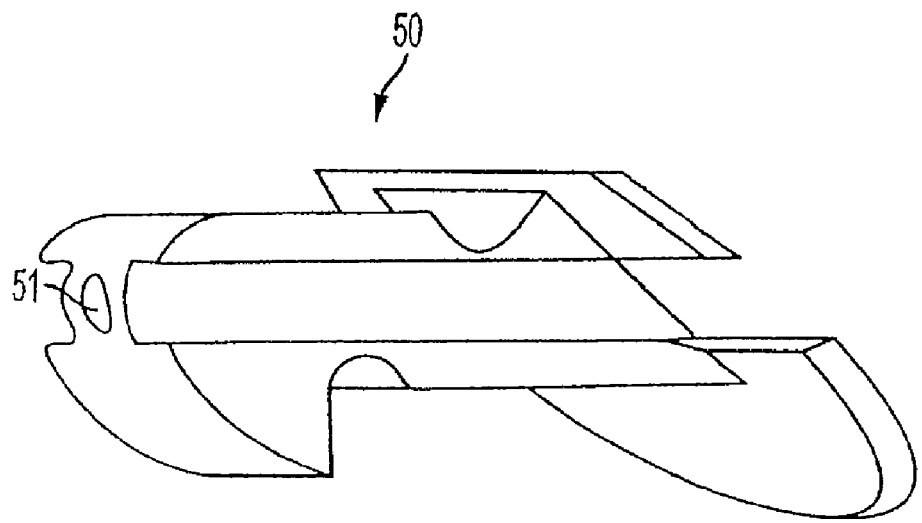
FIG. 10 is a perspective view of an alternative embodiment of a flow regulating implant with side grooves, with a tube passage running through the implant.
Figure 11:
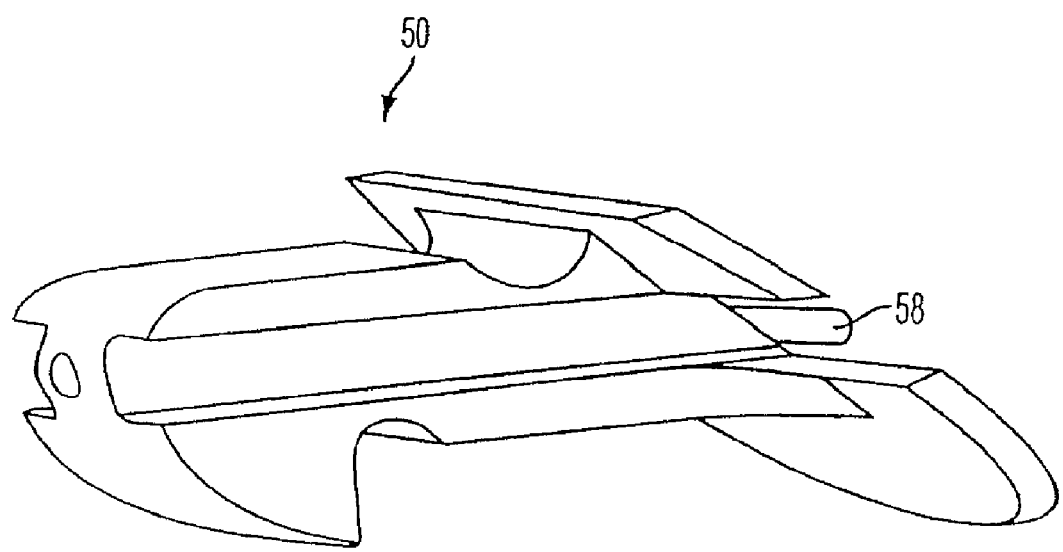
FIG. 11 is a perspective view of the flow regulating implant of FIG. 10, with a thread or suture in the tube passage.

FIG. 10 is a perspective view of an alternative embodiment of a flow regulating implant with side grooves. The implant 50 has tube passage 51 running through the implant. This tube passage 51 provides an additional passageway for fluid flow. The tube passage may have in it absorbable, biodegradable, laser-ablatable and/or removable material for blocking or partially obstructing fluid flow, and for allowing further flow over time. FIG. 11 illustrates the flow regulating implant of FIG. 10, with a thread or suture 58 in the tube passage 51.

Figure 12:
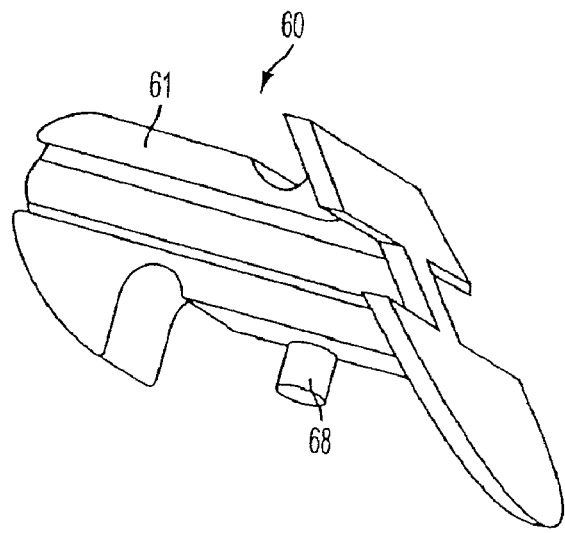
FIG. 12 is a perspective view of an alternative embodiment of a flow regulating implant, with a side pin.

FIG. 12 is a perspective view of an alternative embodiment of a flow regulating implant 60, with a side projection in the form of a side pin 68. Upon implantation, the pin 68 is fixed in the scleral tissue and serves to resist rotation of the device. The pin 68 may also assist in holding the device in the sclera, providing a sealing of the sclera around the shaft of the implant to prevent undesired leakage. The pin also fixes the device to prevent the possibility of the device pressing on and eroding the conjunctiva.

The projection or pin could be may of any suitable material, and it could be removable or changeable. For example, the projection or pin could be made of absorbable, biodegradable, laser-ablatable and/or removable material. The projection or pin 68 could be movable with a hole in the shaft 61, so that its length of projection from the shaft 61 could be adjustable. Also, a slot or other holes could be provided to allow adjustment of the positioning of the projection or pin.

Figure 13:
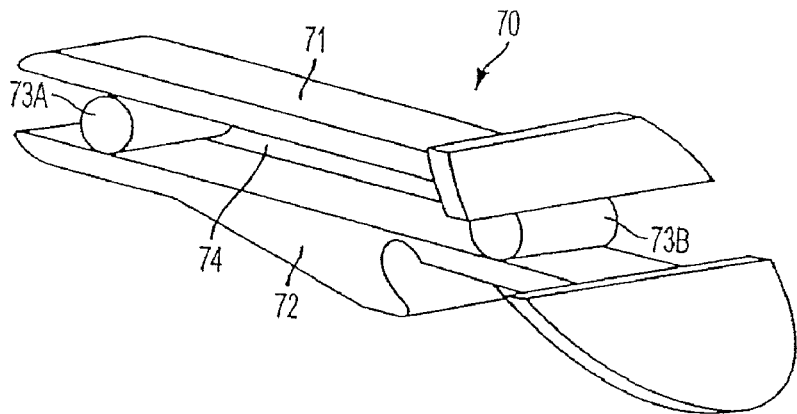
FIG. 13 is a perspective view of an alternative embodiment of a flow regulating implant, comprising two parts that are held at a distance from each other to allow fluid flow between the parts.

FIG. 13 is a perspective view of an alternative embodiment of a flow regulating implant. The implant 70 comprises two parts 71, 72 that are held at a distance from each other to allow fluid flow between the parts. In implant 70, the two parts 71, 72 are joined to each other by two cylinders 73A, 73B. The implant may be formed as one piece, or the parts may be joined by any suitable means, for example welding. The two parts 71, 72 may be joined by just one cylinder or by parts of other shapes, for example, one or more spheres. Alternatively, the two parts may be shaped to be joined directly together with a space between them. It will be appreciated that the space 74 between the parts 71, 72 provides a space for the flow of fluid and allows further fluid contact with the sclera.

Figure 14:
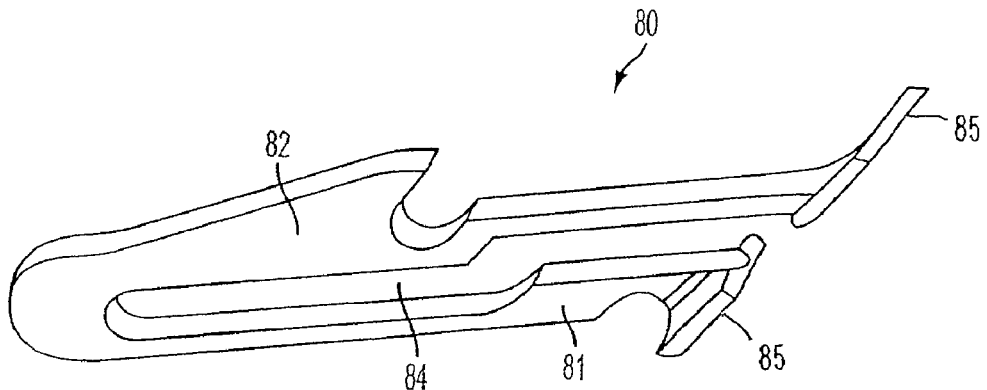
FIG. 14 is a perspective view of an alternative embodiment of a flow regulating implant, comprising two parts that are held at a distance from each other to allow fluid flow between the parts, wherein the two parts may be pushed together or moved apart.

FIG. 14 illustrates a flow regulating implant 80 comprising an elongated portion having two elongated parts 81, 82 that are formed together as parts of a single, one-piece device. As illustrated in FIG. 14 and similar to previous embodiments discussed above, a flange 85 is attached to and projects at an angle with respect to each of the two elongated parts 81, 82. It will be appreciated that the space 84 between the parts 81, 82 provides a space for the flow of fluid and allows further fluid contact with the sclera, similar to the implant 70. The two parts 81, 82 may be pushed together or moved apart, which can control the spacing and thus the fluid flow.

An implant constructed in accordance with the invention may be manufactured entirely from or covered with any suitable material, such as stainless steel, silicon, gold, nitinol, Teflon, tantalum, PMMA, or any other suitable metallic or polymeric or other material. The entire device may be made from a degradable material. The device may be made by molding or any other suitable method of manufacture. The device may be manufactured as one piece or as separate pieces that are joined together. The implant may be coated with heparin or any other suitable coating.

Implants in accordance with the invention may be provided with other features and/or implanted with delivery devices and/or by other methods, for example those disclosed in U.S. Pat. Nos. 5,868,697; 6,203,513 and 6,558,342, discussed above.

As will be appreciated by persons having ordinary skill in the art, the various embodiments of implants described hereinabove are given by way of example only. Various changes, modifications and variations may be applied to the described embodiments without departing from the scope of the invention, defined by the appended claims.

The invention claimed is:

1. A method of implanting an intraocular implant at an implantation site comprising the steps of:
   (a) using an intraocular implant having an inlet end and an outlet end, the intraocular implant comprising:
      (i) an elongated portion comprising a first elongated part and a second elongated part, wherein the first elongated part is separated from the second elongated part to leave a space between the first elongated part and the second elongated part for enabling fluid flow; and
      (ii) a flange attached to at least the first elongated part, the flange being located at the outlet end of the intraocular implant;
   (b) adjusting the spacing between the first elongated part and the second elongated part; and
   (c) inserting the intraocular implant through scleral tissue at the implantation site such that the inlet end of the intraocular implant is located within the anterior chamber of the eye, thereby permitting aqueous humor to flow out of the anterior chamber.

2. The method of claim 1, wherein the flange projects from the first elongated part at an angle with respect to the first elongated part.

3. The method of claim 1, wherein the first elongated part and the second elongated part are formed together as parts of a single, one-piece implant.

4. A method of implanting an intraocular implant at an implantation site comprising the steps of:
   (a) using an intraocular implant having an inlet end and an outlet end, the intraocular implant comprising:
      (i) a shaft, wherein the shaft has one or more grooves in the side of the shaft for enabling fluid flow; and
      (ii) a flange located at the outlet end of the intraocular implant;
   (b) adjusting the spacing between a first elongated part and a second elongated part of the intraocular implant; and
   (c) inserting the intraocular implant through scleral tissue at the implantation site such that the inlet end of the intraocular implant is located within the anterior chamber of the eye, and such that aqueous humor flows out of the anterior chamber and along the one or more grooves toward the outlet end of the implant.

5. The method of claim 4, wherein the cross section of at least one groove is constant along its length.

6. The method of claim 4, wherein at least one groove is tapered.

7. The method of claim 4, further comprising removable material located in at least one groove.

8. The method of claim 7, wherein the removable material is a laser-ablatable materials.

9. The method of claim 7, wherein the removable material is a removable thread or suture.

10. The method of claim 4, further comprising a degradable material located in at least one groove.

11. The method of claim 4, further comprising an absorbable material located in at least one groove.

12. The method of claim 4, further comprising a resilient band or coating covering at least a portion of at least one groove.

13. The method of claim 4, further comprising a projection extending from the side of the shaft for anchoring the implant within tissue.

14. The method of claim 4, wherein the cross-section of the shaft is non-circular.

15. A method of implanting an intraocular implant at an implantation site comprising the steps of:
   (a) using an intraocular implant having an inlet end and an outlet end, the intraocular implant comprising:
      (i) a shaft, wherein the shaft has one or more grooves located on the external surface of the shaft and extending from the inlet end to the outlet end for enabling fluid flow; and
      (ii) a flange located at the outlet end of the intraocular implant;
   (b) adjusting the spacing between a first elongated part and a second elongated part of the intraocular implant; and
   (c) inserting the intraocular implant through scleral tissue at the implantation site such that the inlet end of the intraocular implant is located within the anterior chamber of the eye, thereby permitting aqueous humor to flow out of the anterior chamber.

* * * * *